(12) United States Patent
Rudolf

(10) Patent No.: US 9,395,310 B2
(45) Date of Patent: Jul. 19, 2016

(54) DEVICE FOR IMAGING THE INNER SURFACE OF A CAVITY IN A WORKPIECE

(71) Applicant: Michael Rudolf, Constance (DE)

(72) Inventor: Michael Rudolf, Constance (DE)

(73) Assignee: HOMMEL-ETAMIC GmbH, Villingen-Schwenningen (DE)

( * ) Notice: Subject to any disclaimer, the term of this patent is extended or adjusted under 35 U.S.C. 154(b) by 486 days.

(21) Appl. No.: 13/668,520

(22) Filed: Nov. 5, 2012

(65) Prior Publication Data

US 2013/0112881 A1 May 9, 2013

(30) Foreign Application Priority Data

Nov. 4, 2011 (DE) .................... 10 2011 117 618

(51) Int. Cl.
*G01N 21/954* (2006.01)

(52) U.S. Cl.
CPC .................... *G01N 21/954* (2013.01)

(58) Field of Classification Search
CPC ...... G01T 1/2018; G01T 127/146; G01T 1/20
USPC .......... 250/361; 356/237.2, 241.1–6, 237.1–5
See application file for complete search history.

(56) References Cited

U.S. PATENT DOCUMENTS

| | | | | |
|---|---|---|---|---|
| 4,694,177 A * | 9/1987 | Akai | ..................... | G01T 1/202 250/366 |
| 6,538,371 B1 * | 3/2003 | Duggal | .............. | C09K 11/7774 252/301.4 H |
| 6,621,516 B1 * | 9/2003 | Wasson | .................. | H04N 7/185 348/36 |
| 8,334,971 B2 * | 12/2012 | Keller | .................. | G01N 21/954 356/237.2 |
| 2003/0104232 A1 * | 6/2003 | Kihara et al. | .............. | 428/473.5 |
| 2006/0164733 A1 * | 7/2006 | Gal | ..................... | A61B 1/00177 359/725 |
| 2009/0082629 A1 * | 3/2009 | Dotan | ................ | A61B 1/00096 600/160 |
| 2009/0096413 A1 * | 4/2009 | Partovi | .................... | H01F 5/003 320/108 |

FOREIGN PATENT DOCUMENTS

| | | |
|---|---|---|
| DE | 10 2007 031357 A1 | 3/2009 |
| DE | 10 2008 009975 A1 | 8/2009 |
| DE | 10 2009 019459 A1 | 12/2010 |
| EP | 2 589 953 A2 | 5/2013 |
| WO | 2009/003692 A | 8/2009 |
| WO | 2009/150653 A1 | 12/2009 |

OTHER PUBLICATIONS

German Office Action dated Jun. 29, 2012 in German Patent Application 10 2011 117 618.0 (5 pages).

* cited by examiner

*Primary Examiner* — Casey Bryant
(74) *Attorney, Agent, or Firm* — Shlesinger, Arkwright & Garvey LLP.

(57) ABSTRACT

A device for imaging an inner surface of a cavity in a workpiece includes optics with a panoramic view, and has an image transmission connection with an image sensor and a downstream evaluation device. The device also has an illumination system with a light source for illuminating an imaging region of the inner surface imaged by the optics. Further, at least one light-emitting and/or light-deflecting component of the illumination system is provided on a lens, such as in particular a front lens, of the optics.

23 Claims, 5 Drawing Sheets

DEVICE FOR IMAGING THE INNER SURFACE OF A CAVITY IN A WORKPIECE

CROSS-REFERENCE TO RELATED APPLICATION

This application claims the priority of German application no. 10 2011 117 618.0, filed Nov. 4, 2011, and which is incorporated herein by reference.

FIELD OF THE INVENTION

The invention relates to a device of the type for imaging the inner surface of a cavity in a workpiece.

BACKGROUND OF THE INVENTION

These types of devices are used, for example and in particular, in the automotive industry, to check cylinder bores in crankcases within the scope of quality management, among other things. The devices are used, for example, to image the radial inner surface of a cylinder bore, and to check whether the predetermined requirements for surface quality are met.

Such a device is known from WO 2009/003692. These devices have an optics with a panoramic view, which is in image transmission connection with an image sensor and a downstream evaluation device. The known devices also have an illumination system for illuminating an imaging region of the inner surface imaged by the optics.

A similar device is known from DE 10 2009 019 459 A1, in which the illumination system is provided relative to the optics in such a way, and the beam path of the illumination system is selected in such a way, that a first axial section of the imaging region is illuminable in bright field illumination, and at the same time, another axial section of the imaging region provided at a distance from the first axial section is illuminable in dark field illumination.

A device of the type for imaging the inner surface of a cavity in a workpiece is known from DE 10 2008 009 975 A1, having an optics which is in image transmission connection with an image sensor and a downstream evaluation device. The device has an illumination system with a light source for illuminating an imaging region of the inner surface imaged by the optics. The light source, which may be designed as an LED light source, for example, is provided at an axial distance from the front lens of the optics, and is mechanically connected to the optics via a mounting.

A device designed as a medical endoscope is known from WO 2009/150653 A1, having an optics and a light source for illuminating an imaging region of the inner surface imaged by the optics. The light source is provided on a printed circuit, and is located in the direct proximity of the front lens of the optics.

A medical endoscope is known from US 2009/0082629 A1, having an optics with a front lens which is provided on an optical element whose end facing the lens is designed as a mirror. The mirror bears light-emitting diodes in a ring-shaped configuration which form the light source.

A device for inspecting pipes is known from U.S. Pat. No. 6,621,516 B1, having a panoramic lens mounted on a cart.

A wide-angle imaging assembly is known from US 2006/0164733 A1, having an aspherical optical block, the material of which is selected so that it is transparent for a specific wavelength range. The known optics is provided in particular for use in surveillance cameras.

OBJECTS AND SUMMARY OF THE INVENTION

An object of the invention is to provide a device for imaging the inner surface of a cavity in a workpiece, whose usability is expanded due to a reduced size.

This object is achieved by the invention.

The invention departs from the concept of reducing the dimensions of the components of a device in order to achieve a smaller size.

Rather, the invention is based on the concept of changing the construction of a device for imaging the inner surface of a cavity in a workpiece in order to reduce the size, in particular in one geometric dimension of this device, thus enabling use even in comparatively small cavities.

In the automotive manufacturing sector, for example, increasingly stringent requirements for environmental compatibility are being imposed on internal combustion engines. To be able to meet these requirements, among other measures the cylinder capacity of an engine has been decreased. This decrease in cylinder capacity is often achieved by reducing the diameter of the cylinder bores for the correspondingly adapted pistons of the internal combustion engine. To be able to inspect, for example, the inner surface of these cavities of a crankcase for which the cylinder capacity has been reduced, the invention provides that a lens of the optics carries at least one light-emitting and/or light-deflecting component of the illumination system. According to the invention, at least one light-emitting and/or light-deflecting component is thus attached directly, i.e., without connection of additional components in between, to at least one lens of the optics. In this sense, the light-emitting and/or light-deflecting component includes all of its optical, electrical/electronic, and mechanical components, such as for an LED, for example, its semiconductor component, its optics, and its mounting/holder.

The advantage resulting from a device according to the invention, among others, is that the region of the optics that is relevant for the evaluation may remain free, and in particular is not constrained, for example, by a mounting for a light-emitting and/or light-deflecting component of the illumination system. An associated advantage is that only one image recording of the imaging region imaged by the optics with a panoramic view is necessary to allow the inner surface to be appropriately inspected. This results, among other things, in rapid imaging of the inner surface of an affected cavity in a workpiece, since, for example, further imaging in which the mounting for a light-emitting and/or light-deflecting component of the illumination system is rotated with respect to the optics is dispensed with.

According to the invention, a lens of an optics is understood to mean an optically active component made at least partially of glass or some other transparent medium having optically refractive surfaces, of which at least one surface, for example and in particular, has a convex or concave shape, so that the light passing through the lens is appropriately refracted at this surface. Furthermore, a front lens is understood to mean a lens which in terms of lighting technology refracts the light beams reflected from the inner surface as a first lens of the device. Thus, according to the invention the front lens is understood to mean the lens at the front of the optics, viewed in the direction of insertion of the device into the cavity of the workpiece.

According to the invention, a light-emitting component is understood to mean a component that generates light and/or emits light over at least a portion of its surface to the surroundings to be illuminated.

According to the invention, a light-emitting component may also be formed by an optical fiber, whereby the light source may be provided remotely from the light exit. For example, a light-emitting component may be an optical fiber having a light source associated with the optical fiber, the light source being provided on the end of the optical fiber opposite from the light exit end, thus allowing the light to be conducted through the optical fiber to the light exit end of the optical fiber.

According to the invention, a light-deflecting component is used in particular to change the direction of the light.

According to the invention, light-deflecting components may be formed in particular by mirrors, prisms, diaphragms, and lenses, or a combination of the above-mentioned components.

A light-emitting and/or light-deflecting component may be provided on a lens of the optics in various ways. For example, the above-mentioned component may be glued to the lens, or affixed to the lens by means of a mounting. This mounting may also be substantially directly affixed or directly affixed to the lens by being glued to the lens, for example, or joined in some other way, as shown and described.

Furthermore, the light that is emitted from the light source for illuminating an imaging region of the inner surface imaged by the optics may be guided through a recess, in particular a through opening, in the lens. This may also be achieved, among other ways, using an optical fiber, preferably a glass fiber cable. In addition, the recess may be mirror-coated in order to conduct the light.

To minimize impairment of the detection capability of a device according to the invention for imaging the inner surface of a cavity in a workpiece, another advantageous further embodiment of the invention provides that the light-emitting and/or light-deflecting component is provided outside a field of view of the optics used for imaging the inner surface. For example, for checking the surface quality of a cylinder through hole, imaging over only a partial region of the optics is sufficient for the associated evaluation. Thus, the unused region of the optics may be utilized for holding a light-emitting and/or light-deflecting component without impairing the evaluation. Thus, for example, the optics for checking the inner surface of a cylinder may be provided with a recess on the optical axis or in the region of the optical axis, since this region of the optics is generally not needed for imaging and subsequent evaluation.

Against this background, another advantageous further embodiment of the invention is characterized in that the component is provided in the region of a vertex or at a vertex on the front lens of the optics. As stated above, this results in the advantage that the imaging region of the optics that is relevant for the subsequent evaluation remains free.

As also stated above, in some applications the region around the optical axis (zenith axis) of the optics is irrelevant for the evaluation, so that it is advantageous to provide the light-emitting and/or light-deflecting component in this region. Therefore, one advantageous further embodiment of the invention provides that the light-emitting and/or light-deflecting component is provided on the optical axis or in the region of the optical axis of the optics.

The light-emitting and/or light-deflecting component on the lens, in particular the front lens, of the optics may be geometrically configured in various ways. Thus, the component may be provided at a proximal or distal end of the optics. However, the light-emitting and/or light-deflecting component is advantageously provided at the distal end of the optics, so that, among other things, the light output is not diminished by other optical elements or obstructions, and may thus be directed with low loss onto the imaging region of the inner surface to be imaged. Accordingly, in another advantageous further embodiment of the invention it is provided that the light-emitting and/or light-deflecting component is provided at the distal end of the optics.

According to the invention, a distal end of the optics is understood to mean the front end of the optics in the direction of insertion into the cavity.

For illuminating an imaging region of the inner surface which is imaged by the optics, the light generated by a light source may be deflected in various ways, for which purpose a prism or a lens, among other elements, may be used, as stated above. The light may be deflected in a simple and cost-effective manner using a mirror or multiple mirrors; thus, another advantageous further embodiment of the invention provides that the light-deflecting component has at least one mirror.

The illumination of an imaging region of the inner surface which is imaged by the optics may be achieved in various ways. For example, a light source may be provided at the proximal end of the device, and the light may be conducted by means of an optical fiber to the desired area of the device for the light emission. For example, the heat generation in the region of the lens may thus be reduced in order to decrease imaging or measuring errors.

On the other hand, it is also possible to dispense with light guiding, in that the light-emitting component is a light source element associated with the power supply device. In this regard, the light may be generated in the vicinity of the imaging region of the inner surface to be imaged in order to minimize power losses. To supply this light source element with power, a power supply device is used which may be implemented in the simplest manner possible using an electrical power source and electrical lines connected thereto. These lines may be provided, for example, in a region of the optics that is unimportant for the detection of the imaging region of the inner surface, so that ultimately they may be electrically connected to a light source element. The lines may, for example, be led through a recess, for example a through hole, in the optics, wherein the recess may be located in a spatial region of the optics that is not used for imaging the inner surface.

A light source element may be supplied with power in various ways. Thus, the power required for operating a light source element may be supplied to same in a cabled or also in a wireless manner.

Against this background, one advantageous further embodiment of the invention provides that the power supply device is configured in such a way that power is transmitted or transmittable to the light source element in a wireless manner. This results in the advantage that electrical lines do not have to be guided in a particular way so as not to impair the field of view of the optics. In addition, a modular design of the device may be facilitated in this way.

The transmission of power in a wireless manner may be achieved in various ways, for example by electromagnetic induction. In this regard, another advantageous further embodiment of the invention provides that the power supply device has at least one induction coil system. In this embodiment, the power supply of the light source element is enabled in a contactless manner, in particular even when the light source element has high power requirements. In addition, in this embodiment two or more light source elements may be supplied with electrical power in a particularly simple manner.

In order to leave the field of view of the optics unimpaired by the induction coil system, another advantageous further embodiment of the invention provides that at least one coil of the induction coil system is provided outside a field of view of the optics that is used for imaging the inner surface.

A further embodiment of the above-mentioned embodiment provides that the coil is a receiver coil.

Furthermore, the wireless energy transmission may be at least partially supplemented or replaced by a cabled power supply. In this regard, another advantageous further embodiment of the invention provides that the light source element is connected to the power supply device via at least one supply line. The power supply of the light source element may thus be achieved using a simple means. For example, if the light source element is electrically operated, it is possible to use electrical lines which are guided from the power supply device to the light source element in a region that does not impair the field of view of the optics.

Another further embodiment of the invention provides that at least one electrode for electrically connecting the supply line to the light source element is made of an optically transparent material. An electrode made of an optically transparent or essentially transparent material may be implemented by means of a coating, for example, which is applied to the optics, for example. This option is taken into account in another advantageous further embodiment, in that at least one electrode forms a coating of a lens of the optics. It is possible for the electrode to form a coating, at least in places, of the lens of the optics. The lens may also be coated in segments, which allows various electrodes to be formed on the lens by means of the coating.

Furthermore, it is thus possible to place various electrical consumers in different regions of the optics or the lens, and to supply them with the required power.

An imaging region of the inner surface which is imaged by the optics may be illuminated in various ways. Thus, for example, as stated above, a light source element may be used which may be formed by means of at least one LED, for example.

It is also possible to externally excite the light-emitting component. For this purpose, another advantageous further embodiment of the invention provides that the light-emitting component has at least one luminescent element which generates light when excited by electromagnetic radiation. The excitation for the light emission may occur in various ways. Thus, for example, illumination according to the invention of an imaging region of the inner surface which is imaged by the optics may be achieved by luminescence. In this regard, a fluorescent or phosphorescent body, for example, may be used as the luminescent element according to the invention which generates light when excited by electromagnetic radiation.

In addition, another advantageous further embodiment of the invention is provided in that the illumination system is provided relative to the optics in such a way, and the beam path of the illumination system is selected in such a way, that a first axial section of the imaging region is illuminated or illuminable in bright field illumination, and at the same time, a second axial section of the imaging region provided at a distance from the first axial section is illuminated or illuminable in dark field illumination.

This results in the advantage that an imaging region of the inner surface which is imaged by the optics may be illuminated partially in bright field illumination and partially in dark field illumination. In bright field illumination, in which the light reflected from the inner surface to be imaged is used for the imaging, this results in particularly high-contrast imaging by means of which, for example and in particular, scratches and porosities in the inner surface to be imaged may be detected. On the other hand, in dark field illumination, in which the beam path of the light is guided in such a way that primarily beams that are scattered at the inner surface to be imaged are used for the imaging in order to detect other structural defects, for example casting defects of cast parts. In this regard it is possible to image the inner surface to be imaged in bright field illumination as well as in dark field illumination. A device configured in this way thus combines the existing advantages of both illumination methods with regard to the detection of defects.

However, in an appropriately configured device according to the invention it is possible to image the same axial section of the inner surface to be imaged in succession, in dark field illumination as well as in bright field illumination. For example, for this purpose an advancing apparatus may be dedicated to the device, by means of which the device is axially movable relative to the inner surface to be imaged. If, for example, a section of the inner surface examined in dark field illumination is inclined at an angle in front of the optics in the advancing direction, while a section examined in bright field illumination is located approximately at the level of the optics or slightly behind same in the axial direction of the cavity, during the advance a predetermined axial region of the inner surface may be initially imaged in dark field illumination, and during a further advance of the device, may be subsequently imaged in bright field illumination.

The subject matter of the invention also includes a combination of an illumination system according to the invention, in which a light-emitting and/or light-deflecting component is provided on a lens of the optics, with an illumination system known from DE 10 2009 019 459 A1, in which a light-emitting or light-deflecting component is provided not on a lens of the optics, but instead on another component of the device. The subject matter of the DE 10 2009 019 459 A1 illumination system is incorporated herein by reference, and the subject matter is as set forth in counterpart U.S. Publication No. 2011/0001984 A1 to Keller et al., published Jan. 6, 2011, and which is incorporated herein by reference.

The basic concept according to the invention, to provide a light-emitting or light-deflecting component on a lens, in particular a front lens, of the optics, may also be used in general in imaging devices which have an optics and an image sensor. In this case, a downstream evaluation device as well as an illumination system are not necessarily present.

The invention is explained in greater detail below with reference to the appended drawings, which illustrate highly schematic embodiments of a device according to the invention. All features described, illustrated in the drawings, and claimed in the patent claims constitute the subject matter of the invention, alone or in any given technically reasonable combination, independently of their combination in the patent claims or their dependencies, and independently of their description or illustration in the drawings.

The term "x and/or y" will be understood to mean "one of x and y," namely "at least one of x and y."

Relative terms such as up, down, left, and right are for convenience and are not intended to be limiting.

For the sake of clarity, the illustrations in the figures are reduced to the elements which assist in understanding. Identical or corresponding components or elements are provided with the same reference numerals in the figures.

DETAILED DESCRIPTION OF THE INVENTION

Figure 1:
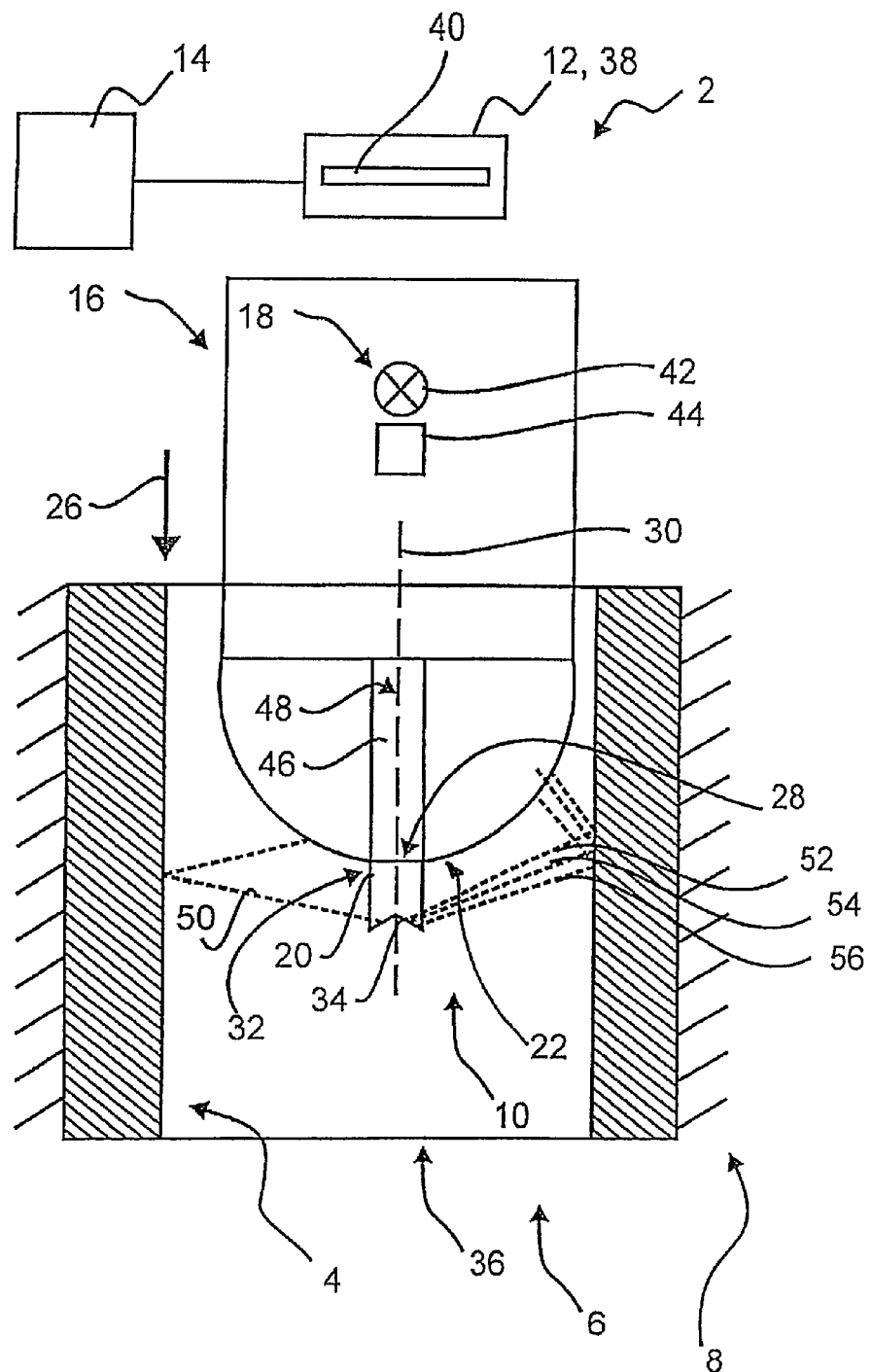
FIG. 1 shows a schematic side view of a first embodiment of a device according to the invention, in the imaging position.
Figure 2:
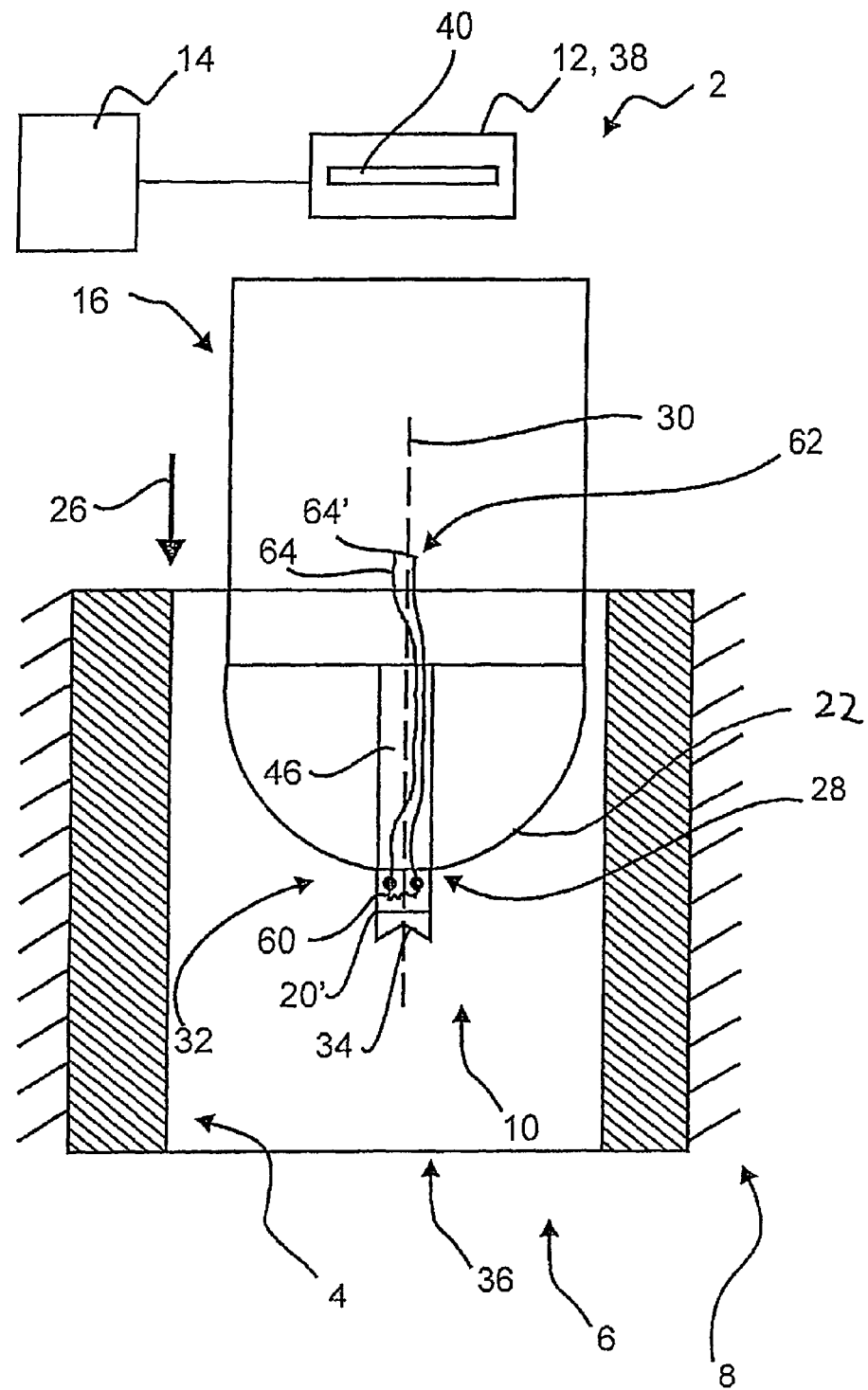
FIG. 2 shows a second embodiment of a device according to the invention, in the same manner of illustration as in FIG. 1.

FIG. 1 illustrates, in a highly schematic manner, a side view of a first embodiment of a device 2 according to the invention for imaging an inner surface 4 of a cavity 6 in a workpiece 8. The device 2 has an optics or optical system 10 with a panoramic view, which has an image transmission connection with an image sensor 12 and a downstream evaluation device 14. In other words, there is an image transmission connection of the optics with the image sensor, and that image transmission connection of the optics with the image sensor may be termed an optical connection, as will be readily apparent to a person having ordinary skill in the art. The image sensor 12 and downstream evaluation device 14 have an image transmission connection as shown in FIG. 2, for example. The device 2 also has an illumination system 16 with a light source 18 for illuminating an imaging region of the inner surface 4 imaged by the optics 10. For illumination, in this embodiment a light-deflecting component 20 is provided which is provided on a lens, which in the present case is a front lens 22, of the optics 10.

In this embodiment the front lens 22 carries the light-deflecting component 20. In addition, the light-deflecting component 20 is provided outside a field of view of the optics 10 which is used for imaging the inner surface 4. The light-deflecting component 20 is provided in the region of the vertex 28 of the front lens 24, in particular in such a way that the light-deflecting component 20 is provided on the optical axis 30 (zenith axis) of the optics 10. In addition, due to the above-mentioned configuration the light-deflecting component 20 is provided at the distal end 32 of the optics 10.

In this embodiment, the light-deflecting component 20 is formed by a mirror 34 which appropriately distributes the light beams striking the mirror in order to illuminate the imaging region of the inner surface 4 to be imaged.

Furthermore, in this embodiment the illumination system 16 is provided relative to the optics 10 in such a way, and its beam path is selected in such a way, that a first axial section of the imaging region is illuminated in bright field illumination, and at the same time, a second axial section of the imaging region provided at a distance from the first axial section is illuminated in dark field illumination.

The optics 10 is configured in such a way that it allows a panoramic view of 360° in order to completely cover the cavity 6, which in the present embodiment is a cylinder 36, in its circumferential direction.

In the present embodiment, the image sensor 12 is configured as a digital camera 38 having an image sensor 40.

In the embodiment illustrated in FIG. 1, the optics 10 is a fisheye lens which images strictly by optical refraction.

In the illustrated embodiment, the optics 10, with the exception of the angular range in which the light-deflecting component 20 is provided, has a viewing angle of >180°, namely, approximately 185°, so that the optics 10 covers not only a region of the inner surface 4 provided obliquely in front of the front lens 24 of the optics 10, but also a region of the inner surface 4 provided farther back with respect to the front lens 24 of the optics 10, along the optical axis 30.

In the illustrated embodiment, the image sensor 40 is configured for covering the entire image circle of the optics 10. Images of the inner surface 4 received by the optics 10 are recorded by the image sensor 40 of the image sensor 12 and stored in a memory device, not illustrated.

For illumination of the imaging region of the inner surface 4, a light source 18 is provided, which in the present embodiment is formed by an LED 42 which has a downstream light beam forming element 44 for orienting the light beams emitted by the LED 42 essentially in parallel, and which is provided remotely from the light-deflecting component 20.

In order to guide the light beams, which are emitted by the LED 42 and oriented by the light beam forming element 44, to the light-deflecting component 20, the front lens 24 has a recess 46 through which the light beams are guided to the light-deflecting component 20.

The inner surface 48 of the recess 46 is solely mechanically machine finished. However, the recess 46 may also have, for example, a reflective coating at the inner surface 48.

In the present embodiment, the recess 46 is formed by a through hole through the front lens 24, the axis (not illustrated) of the through hole coinciding with the optical axis 30 of the optics 10. After passing through the recess 46, the light beams generated by the LED 42 strike the mirror 34, which has a geometric shape which makes possible the above-mentioned bright field and dark field illumination. The light beams emitted by the LED 42 are deflected via the mirror 34 onto the inner surface 4 of the cavity 6, and are reflected from same. For imaging the inner surface 4, a first partial beam 50 strikes the inner surface 4 in such a way that a first axial section of the inner surface 4 is illuminated in bright field illumination. A representation of this type of illumination is symbolically illustrated in FIG. 1 with reference to the partial beam 50. The reflection of the partial beams 52, 54, and 56 on the inner surface is symbolically illustrated in FIG. 1 as a representation of the dark field illumination.

During the advance of the device 2 relative to the workpiece 8, different axial regions of the inner surface 4 are imaged in succession, and in the evaluation device 14 are converted into images which in each case correspond to a flat projection of the inner surface 4.

Further information concerning bright field and dark field illumination may be obtained from DE 10 2009 019 459 A1 and its counterpart US 2011/0001984 A1, and each of which is incorporated herein by reference, discussed above. In addition, information concerning how the evaluation device 14 converts the regions imaged on the image sensor 40 into a Cartesian image may be obtained from DE 10 2007 031 358 A1, and its counterpart WO 2009/003692 A1 to Keller, published Jan. 8, 2009, for example. The respective disclosed content of DE 10 2009 019 459 A1 and DE 10 2007 031 358 A1 cited above is hereby incorporated by reference into the present patent application.

Based on the images recorded in the bright field system and the dark field system, it may be determined whether the inner surface 4 to be examined meets predetermined requirements for surface quality.

For the sake of clarity, in the following only the differences from the first embodiment in FIG. 1 are discussed for the figures described below.

FIG. 2 shows a second embodiment of a device 2 according to the invention, in which a light-emitting and light-deflecting component 20' is provided at the vertex 28 of the front lens 22. For generating the light that is required for illumination of the inner surface 4, the component 20' has a light source element 60 which is associated with the power supply device 62.

Supply lines 64, 64' are used to supply power to the light-emitting and light-deflecting component 20', and in this embodiment are formed in a simple and cost-effective manner by electrical supply lines 64, 64' which supply the light-emitting and light-deflecting component 20' with the electrical power necessary for operating the light source element 60.

The supply lines 64, 64' are guided through the front lens 24 via the recess 46. The recess 46 is configured once again as a cylindrical through hole through the front lens 24.

For the transmission of power, the supply lines 64, 64' are electrically connected to an electrical power source (not illustrated) and to the light-emitting and light-deflecting component 20'.

Figure 3:
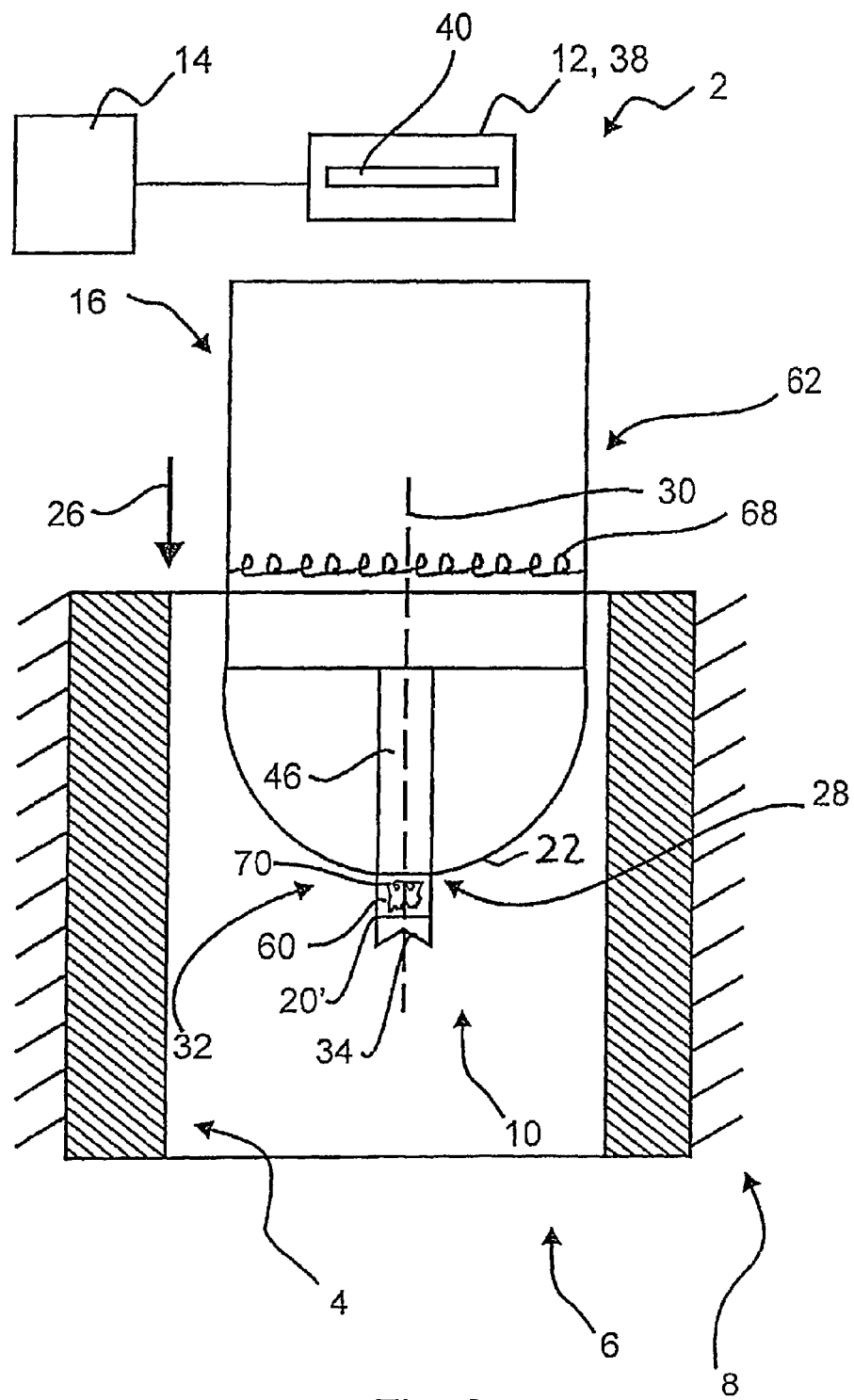
FIG. 3 shows a third embodiment of a device according to the invention, in the same manner of illustration as in FIG. 1.

FIG. 3 shows a third embodiment of a device 2 according to the invention, in which the light-emitting and light-deflecting component 20' is supplied with power for the light generation by means of induction. For this purpose, the power supply device 62 has an induction coil system 66 having a transmitter coil 68 and a receiver coil 70.

Figure 4:
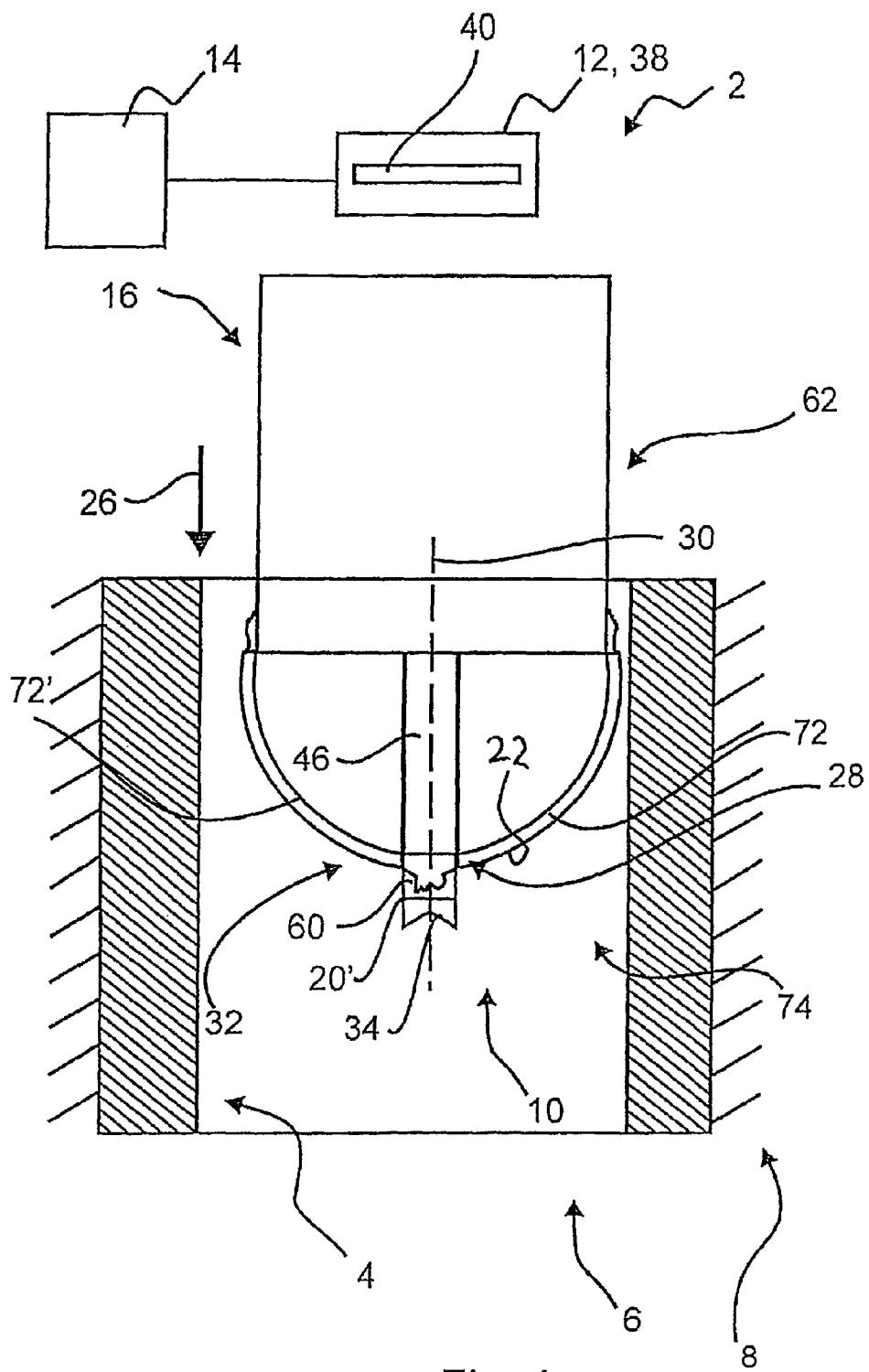
FIG. 4 shows a fourth embodiment of a device according to the invention, in the same manner of illustration as in FIG. 1.

FIG. 4 shows a fourth embodiment of a device 2 according to the invention, in which electrodes 72, 72' for electrically connecting the respective supply line 64, 64' to the light source element 60 are each made of an optically transparent material. The electrodes 72, 72' form a coating 74 of the front lens 24.

Figure 5:
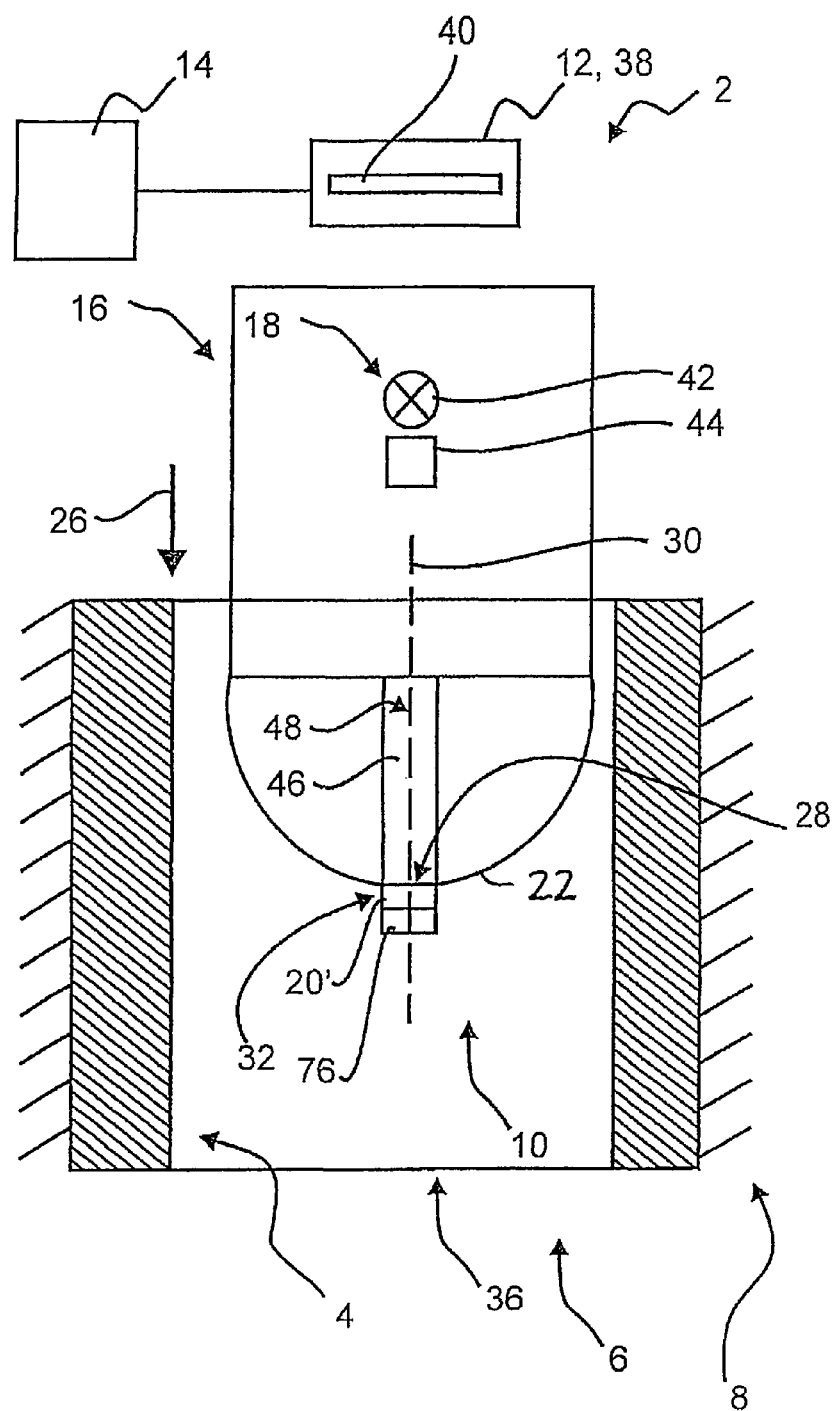
FIG. 5 shows a fifth embodiment of a device according to the invention, in the same manner of illustration as in FIG. 1.

FIG. 5 shows a fifth embodiment of a device 2 according to the invention. The light-emitting component 20 has a luminescent element 76 which generates light when excited with electromagnetic radiation. The electromagnetic radiation may be generated in the form of light as in the first embodiment, by means of a light source 18 which is provided remotely from the luminescent element 76, and which once again may be formed by an LED 42. The light generated by the LED 42 may be guided to the luminescent element 76 in the same way as in the first embodiment, by means of a recess 46 in the front lens 24. The luminescent element 76 has a phosphorescent material for generating light.

One possible modification of the embodiment according to FIG. 5 is to dispense with the recess 46, and to guide the light directly through the optical axis of the optics 10 to the luminescent element 76. Any beam deformation which may occur may be compensated for by means of the light beam forming element 44. In the embodiment according to FIG. 5 as well as in the above-described modification, an optical filter may be provided in front of the image sensor 12 which allows the light to pass from the luminescent element 76 unhindered or essentially unhindered, but blocks the light emitted by the light source 18. In this way, scattered light from the illumination is prevented from reaching the image sensor 12. This modification is based on the consideration that the light that is generated by the luminescent element 76 is generally light having a longer wavelength than the light emitted by the light source 18.

While this invention has been described as having a preferred design, it is understood that it is capable of further modifications, and uses and/or adaptations of the invention and following in general the principle of the invention and including such departures from the present disclosure as come within the known or customary practice in the art to which the invention pertains, and as may be applied to the central features hereinbefore set forth, and fall within the scope of the invention.

What is claimed is:

1. Device for imaging an inner surface of a cavity in a workpiece, comprising:
   a) an optics, and an image sensor having a downstream evaluation device;
   b) the optics having an image transmission connection with the image sensor, and the image sensor having an image transmission connection with the downstream evaluation device;
   c) an illumination system, the illumination system including a light source for illuminating an imaging region of the inner surface which is imaged by the optics;
   d) the illumination system including one of a light-emitting and a light-deflecting component; and
   e) the optics including a front lens, the front lens having a distal end, and the one of the light-emitting and light-deflecting component of the illumination system being substantially directly affixed to the distal end of the front lens.

2. Device according to claim 1, wherein:
   a) the one of the light-emitting and light-deflecting component is provided outside a field of view of the optics which is used for imaging the inner surface.

3. Device according to claim 1, wherein:
   a) the one of the light-emitting and light-deflecting component is provided in the region of or at a vertex on the lens of the optics.

4. Device according to claim 1, wherein:
   a) the one of the light-emitting and light-deflecting component is provided on or in the region of an optical axis of the optics.

5. Device according to claim 1, wherein:
   a) the light-deflecting component includes at least one mirror.

6. Device according to claim 1, wherein:
   a) the light-emitting component includes a light source element with which a power supply device is associated.

7. Device according to claim 6, wherein:
   a) the power supply device is configured in such a way that power is transmitted or is transmittable to the light source element in a wireless manner.

8. Device according to claim 7, wherein:
   a) the power supply device includes at least one induction coil system.

9. Device according to claim 8, wherein:
   a) at least one coil of the induction coil system is provided outside a field of view of the optics that is used for imaging the inner surface.

10. Device according to claim 9, wherein:
    a) the at least one coil is a receiver coil.

11. Device according to claim 6, wherein:
    a) the light source element is connected to the power supply device via at least one supply line.

12. Device according to claim 11, wherein:
    a) an electrode for electrically connecting the at least one supply line to the light source element is provided and is made of an optically transparent material.

13. Device according to claim 12, wherein:
    a) the electrode includes at least one electrode which forms a coating of the lens of the optics.

14. Device according to claim 1, wherein:
    a) the light-emitting component includes at least one luminescent element which generates light when excited by electromagnetic radiation.

15. Device according to claim 1, wherein:
    a) the illumination system is provided relative to the optics in such a way, and a beam path of the illumination system is selected in such a way, that a first axial section of the imaging region is illuminated or is illuminable in bright field illumination, and at the same time, a second axial section of the imaging region provided at a distance from the first axial section is illuminated or is illuminable in dark field illumination.

16. Device according to claim 1, wherein:
a) the optics has a panoramic view.

17. Device according to claim 1, wherein:
a) the one of the light-emitting and light-deflecting component affixed at the distal end of the front lens is the light-emitting component.

18. Device according to claim 17, wherein:
a) the light-emitting component includes a light source element with which a power supply device is associated.

19. Device according to claim 1, wherein:
a) the one of the light-emitting and light-deflecting component affixed at the distal end of the front lens is the light-deflecting component.

20. Device according to claim 1, wherein:
a) the light-deflecting includes at least one mirror.

21. Device according to claim 1, wherein:
a) the one of the light-emitting and light-deflecting component substantially directly affixed at the distal end of the front lens is the light-emitting component; and
b) the light-emitting component is directly affixed at the distal end of the front lens.

22. Device according to claim 1, wherein:
a) the one of the light-emitting and light-defecting component substantially directly affixed at the distal end of the front lens is the light-deflecting component; and
b) the light-deflecting component is directly affixed at the distal end of the front lens.

23. Device according to claim 1, wherein:
a) the image transmission connection of the optics with the image sensor is an optical connection.

* * * * *